(12) United States Patent  
Urry

(10) Patent No.: US 6,328,996 B1  
(45) Date of Patent: Dec. 11, 2001

(54) BIOELASTOMERIC DRUG DELIVERY SYSTEM

(75) Inventor: Dan W. Urry, Birmingham, AL (US)

(73) Assignees: Bioelastics Research Ltd.; UAB Research Foundation, both of Birmingham, AL (US)

( * ) Notice: Subject to any disclaimer, the term of this patent is extended or adjusted under 35 U.S.C. 154(b) by 0 days.

(21) Appl. No.: 08/316,802

(22) Filed: Oct. 3, 1994

Related U.S. Application Data

(63) Continuation of application No. 07/962,608, filed on Oct. 16, 1992, which is a continuation of application No. 07/846,977, filed on Mar. 6, 1992, now abandoned, which is a continuation of application No. 07/499,697, filed on Mar. 27, 1990, now abandoned.

(51) Int. Cl.[7] .............................. A61K 9/14; A61K 9/10; A61K 47/42
(52) U.S. Cl. ........................... 424/499; 424/486
(58) Field of Search ................... 424/484, 426, 424/486, 499, 78, 35; 514/963, 952, 15, 17, 18; 530/328, 330

(56) References Cited

U.S. PATENT DOCUMENTS

| | | | |
|---|---|---|---|
| 3,867,520 | 2/1975 | Mori et al. | 424/36 |
| 3,888,975 | * 6/1975 | Ramwell | 424/433 |
| 4,178,361 | * 12/1979 | Cohen et al. | 424/487 |
| 4,187,852 | 2/1980 | Urry et al. | 128/334 R |
| 4,351,337 | 9/1982 | Sidman | 128/260 |
| 4,474,851 | 10/1984 | Urry et al. | 428/373 |
| 4,589,882 | * 5/1986 | Urry | 424/423 |
| 4,605,413 | 8/1986 | Urry et al. | 623/11 |
| 4,671,954 | * 6/1987 | Goldberg et al. | 514/963 |
| 4,693,718 | 9/1987 | Urry et al. | 623/11 |
| 4,741,872 | * 5/1988 | DeLuca et al. | 424/501 |
| 4,863,735 | 9/1989 | Khon et al. | 424/422 |
| 4,898,926 | * 2/1990 | Urry | 528/328 |

FOREIGN PATENT DOCUMENTS

| | | |
|---|---|---|
| 27 23 908 A1 | 5/1977 | (DE) . |
| 31 04 815 A1 | 2/1981 | (DE) . |
| 03 49 428 A1 | 6/1989 | (EP) . |

OTHER PUBLICATIONS

ACS Abstract CA 13–59817(7), Chang et al, 1989.*  
ACS Abstract CA14–139219 (15), Castiglione—Morglli et al, 1990.*  
ACS Abstract CA08–22274(3), Rahman et al 1987.*

* cited by examiner

*Primary Examiner*—Edward J. Webman  
(74) *Attorney, Agent, or Firm*—Cooley Godward LLP; Richard L. Neeley

(57) ABSTRACT

A drug delivery composition, comprising a bioelastic polymer, comprising monomeric units selected from the group consisting of bioelastic pentapeptides, tetrapeptides, and nonapeptides, and a drug retained by the polymer, wherein the polymer is selected to be in a first contraction state, selected from the group consisting of contracted and relaxed bioelastomer states, when contacted with a physiological condition present in a human or animal to whom the composition is administered and wherein the polymer contains a reactive functional group that undergoes a reaction, either in the presence of the physiological condition or when the polymer is transported by a natural process in the human or animal to a different location having a different physiological condition, to produce a second functional group, wherein the presence of the second functional group in the polymer causes the polymer to switch to the other of the contraction states, thereby making the drug available for release from the composition.

34 Claims, 6 Drawing Sheets

Cooperativity and pK shifts in Sufficiently Hydrophobic Matrices Capable of Mechanochemical Coupling A. Anionic Chemical Couple (e.g. COOH/COO⁻)

B. Cationic Chemical Couple (e.g. imidazolium/imidazole, His⁺/His)

Fibroblast Migration with $X^{20}$-P(NP)P Doped with H-GFGVGAGVP-OH

BIOELASTOMERIC DRUG DELIVERY SYSTEM

CROSS REFERENCE TO RELATED APPLICATIONS

This application is a continuation of U.S. application Ser. No. 07/962,608, filed Oct. 16, 1992, which is a continuation of U.S. application Ser. No. 07/846,977 filed Mar. 6, 1992, now abandoned, which is a continuation of U.S. application Ser. No. 07/499,697, filed Mar. 27, 1990, now abandoned.

TECHNICAL FIELD

The present invention is directed to the field of bioelastomeric polymers and to uses thereof.

BACKGROUND

Bioelastic polypeptides are a relatively new development that arose in the laboratories of the present inventor and which are disclosed in a series of previously filed patents and patent applications. For example, U.S. Pat. No. 4,474,851 describes a number of tetrapeptide and pentapeptide repeating units that can be used to form a bioelastic polymer. Specific bioelastic polymers are also described in U.S. Pat. Nos. 4,132,746; 4,187,852; 4,500,700; 4,589,882; and 4,870,055. Bioelastic polymers are also disclosed in related patents directed to polymers containing peptide repeating units that are prepared for other purposes but which can also contain bioelastic segments in the final polymer; see U.S. Pat. No. 4,605,413. A number of other bioelastic materials and methods for their use are described in U.S. patent applications including the following: "Bioelastomer containing Tetra/Pentapeptide Units," U.S. Ser. No. 062,557, filed Jun. 15, 1987, now U.S. Pat. No. 4,898,926; "Reversible Mechanochemical Engines Comprised of Bioelastomers," U.S. Ser. No. 410,018, filed Sep. 20, 1989, now issued as U.S. Pat. No. 5,032,271; "Bioelastomeric Materials Suitable for the Protection of Wound Repair Sites," U.S. Ser. No. 184,407, filed Apr. 21, 1988, now issued as U.S. Pat. No. 5,250,516; "Elastomeric Polypeptides as Vascular Prosthetic Materials," U.S. Ser. No. 184,873, filed Apr. 22, 1988; now U.S. Pat. No. 5,336,256 ; "Polynonapeptide Bioelastomers having an Increased Elastic Modulus," U.S. Ser. No. 314,115, filed Feb. 23, 1989, now issued as U.S. Pat. No. 5,064,430. All of these patents and patent applications are herein incorporated by reference, as they describe in detail bioelastomers that can be used in the compositions and methods of the present invention. These bioelastic materials have been proposed for a number of uses, as indicated by the general subject matter of the applications and patents as set forth above.

The present invention is directed to a new use of bioelastic materials, namely as part of a drug delivery system that can be finely tuned so that drug is released in a particular environment.

In the past, compositions used for selective drug delivery have been prepared by designing a particular composition that reacts chemically at a preselected rate that depends on the environment in which the composition is found. For example, a coating which is resistant to acid but which dissolves under basic conditions can be applied to a capsule so that the capsule passes through the stomach of a subject to whom the capsule is administered and dissolves in the intestine of that subject (an enteric-coated capsule). Although such materials have proven suitable for a number of uses, there is a continued need for advances in drug delivery systems.

RELEVANT LITERATURE

In addition to the patents and patent applications cited above, a number of publications in the scientific literature are relevant to the present invention. These publications are listed below, and reference is made in the following specification to these literature references by giving the reference number in parentheses at the location where the reference is being cited.

1. Urry, D. W.: *J. Protein Chem.* 7, 1–34 (1988).
2. Urry, D. W.: *J. Protein Chem.* 7, 81–114 (1989).
3. Urry, D. W.: *American Chemical Society, Div. of Polymeric Materials: Sci. and Engineering* 62 (1990).
4. Hollinger, J. O., J. P. Schmitz, R. Yaskovich, M. M. Long, K. U. Prasad, and D. W. Urry: *Calacif. Tissue Int.* 42, 231–236 (1988)
5. Urry, D. W.: *Intl. J. Quantum Chem.: Quantum Biol. Symp.* 15, 235–245 (1988).
6. Edsall, J. T. and H. A. McKenzie: *Adv. Biophys.* 16, 53–183 (1983).
7. Kauzman, W.: *Adv. Protein Chem.* 14, 1–63 (1959).
8. Urry, D. W., C-H Luan, R. Dean Harris, and Karl U. Prasad: *Polymer Preprint Am. Chem. Soc. Div. Polym. Chem.* (1990).
9. Urry, D. W.: *J. Protein Chem.* 3, 403–436 (1984).
10. Chang, D. K., C. M. Venkatachalam, K. U. Prasad, and D. W. Urry; *J. of Biomolecular Structure & Dynamics* 6, 851–858 (1989).
11. Chang, D. K. and D. W. Urry: *J. of Computational Chemistry* 10, 850–855 (1989).
12. Urry, D. W., B. Haynes, H. Zhang, R. D. Harris, and K. U. Prasad: *Proc. Natl. Acad. Sci. USA* 85, 3407–3411 (1988).
13. Urry, D. W., Shao Qing Peng, Larry Hayes, John Jaggard, and R. Dean Harris: *Biopolymers* (1990).
14. Sidman, K. R., W. D. Steber, and A. W. Burg: In *Proceedings, Drug Delivery Systems* (H. L. Gabelnick, Ed.), DHEW Publication No. (NIH) 77, -1238, 121–140 (1976).
15. Urry, D. W., D. K. Chang, H. Zhang, and K. U. Prasad: *Biochem. Biophys. Res. Commun.* 153, 832–839 (1988).
16. Robinson, A. B.: *Proc. Nat. Acad. Sci. USA* 71, 885–888 (1974).
17. Urry, D. W.: In *Methods in Enzymology,* (L. W. Cunningham and D. W. Frederiksen, Eds.) Academic Press, Inc. 82, 673–716 (1982).
18. Urry, D. W., John Jaggard, R. D. Harris, D. K. Chang, and K. U. Prasad: In *Progress in Biomedical Polymers* (Charles G. Gebelein and Richard L. Dunn, Eds.), Plenum Publishing Co. (1990).
19. Urry, D. W., J. Jaggard, K. U. Prasad, T. Parker, and R. D. Harris: Plenum Press (1990).
20. Urry, D. W., R. D. Harris, and K. U. Prasad: *J. Am. Chem. Soc.* 110, 3303–3305 (1988).
21. Sciortino, F., M. U. Palma, D. W. Urry, and K. U. Prasad: *Biochem. Biophys. Res. Commun.* 157, 1061–1066 (1988).
22. Sciortino, F., D. W. Urry, M. U. Palma, and K. U. Prasad: *Biopolymers* (1990).
23. Pitt, C. G. and A. Schindler, In *Progress in Contraceptive Delivery Systems* (E. Hafez and W. Van Os, Eds.), MTP Press Limited 1, 17–46 (1980).

SUMMARY OF THE INVENTION

It is an object of the present invention to provide a drug delivery system that can be finely tuned to release a drug at a predetermined rate upon the existence of a set of predetermined conditions in contact with the drug-containing composition.

It is a further object of this invention to provide a drug delivery system that can rapidly release a unit dose of drug upon a relatively small change in physiological conditions.

It is still another object of the invention to provide a drug-containing composition which can be implanted and programmed to release drug over a predetermined period ranging from days to decades depending on the particular composition selected for the matrix portion of the system.

These and other objects of the present invention as will hereinafter become more readily apparent have been accomplished by providing a drug delivery composition comprising a bioelastic polymer, comprising elastomeric units selected from the group consisting of bioelastic pentapeptides, tetrapeptides, and nonapeptides, in the form of a solid matrix, and a drug contained in the matrix. By selecting the side chains present in the polymer portion of the composition, fine control is possible over both the drug release rate and the location at which drug is released in an human or animal body.

DESCRIPTION OF THE DRAWINGS

The present invention will be better understood by reference to the following detailed description of the invention and the drawings which form part of the present specification, wherein.

DESCRIPTION OF THE SPECIFIC EMBODIMENTS

Figure 1:
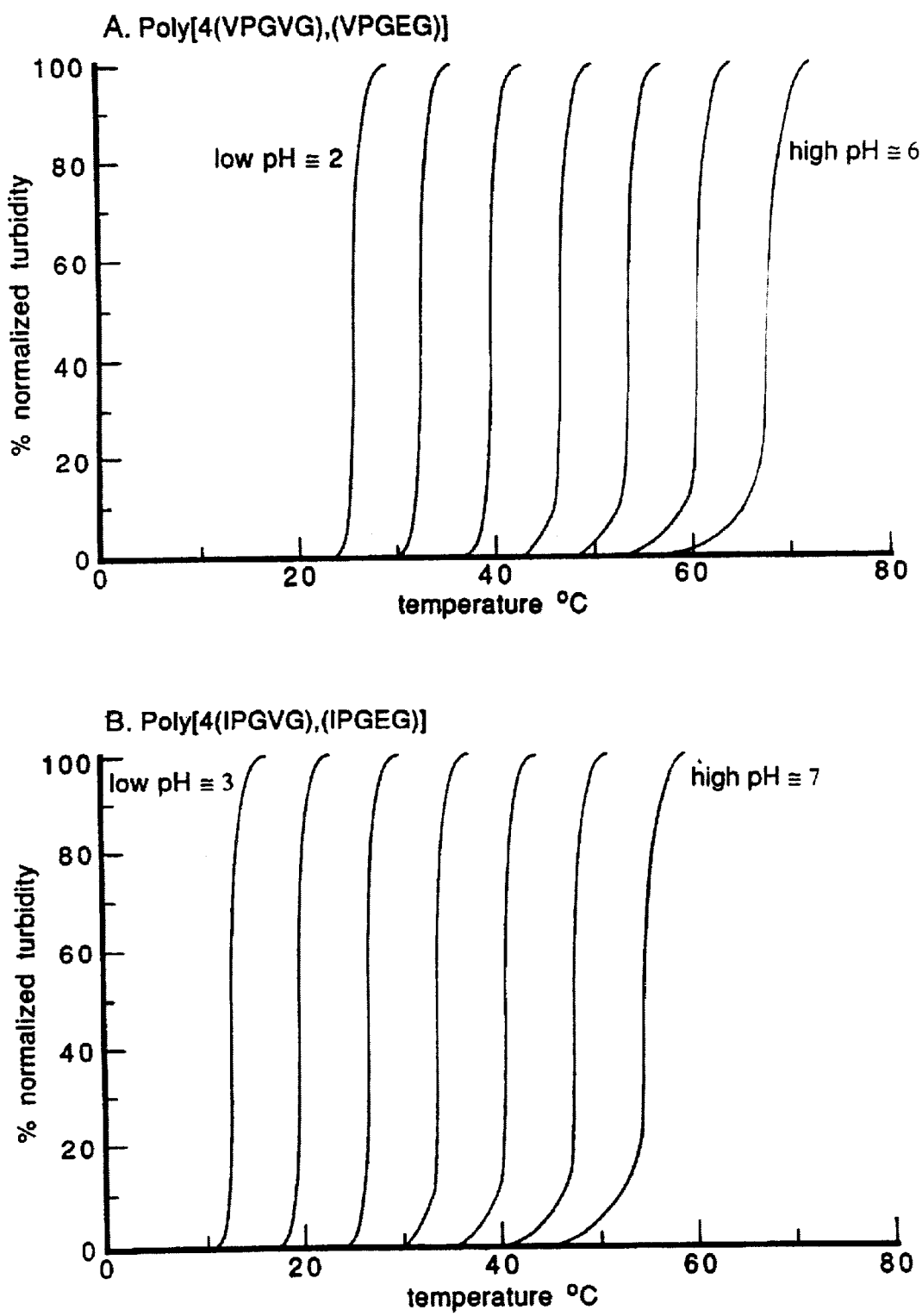
FIG. 1 is a graph showing chemical modulation of inverse temperature transitions and chemomechanical transduction for polymers used in compositions of the present invention.

The present invention provides new uses for and new compositions containing bioelastic polypeptides. Bioelastic polypeptides have been fully characterized and described in a number of patents and patent applications described above. These materials contain either tetrapeptide, pentapeptide, or nonapeptide monomers which individually act as elastomeric units within the total polypeptide containing the monomeric units. The elasticity of the monomeric units is believed to be due to a series of β-turns in the protein's secondary structure, i.e., the conformation of its peptide chain, separated by dynamic (as opposed to rigid) bridging segments suspended between the β-turns. A β-turn is characterized by a 10-atom hydrogen-bonded ring of the following formula:

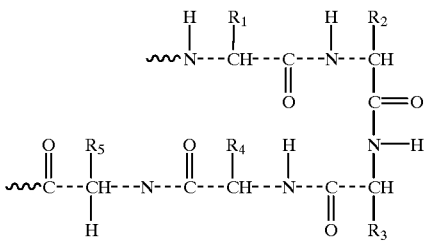

In this formula $R_1$–$R_5$ represent the side groups of the respective amino acid residues. The 10-atom ring consists of the carbonyl oxygen of the first amino acid, the amino hydrogen of the fourth amino acid, and the intervening backbone atoms of amino acids two and three. In this monomeric unit as shown, the remaining backbone atoms of the chain (the remainder of amino acid four, amino acid five, and the first part of amino acid one of the next pentameric unit) form the bridging segment that is suspended between adjacent β-turns.

This β-turn-containing structure is described in the prior patents and patent applications cited above and need not be described again in detail. Considerable variations in the amino acids that are present at various locations in the repeating units is possible as long as the multiple β-turns with intervening suspended bridging segments are retained in order to preserve elasticity. Furthermore, it is possible to prepare polypeptides in which these monomeric units are interspersed throughout a larger polypeptide that contains peptide segments designed for other purposes. For example, rigid segments can be included to increase the modulus of elasticity or segments having biological activity (such as chemotaxis) can be included for their biological activity.

These elastomeric materials, which include the prototypic poly($Val^1$-$Pro^2$-$Gly^3$-$Val^4$-$Gly^5$) and poly($Val^1$-$Pro^2$-$Gly^3$-$Gly^4$) molecules as well as numerous analogues, when combined with water form viscoelastic phases which when cross-linked result in soft, compliant, elastomeric matrices (1–3). The VPGVG-based polypentapeptide (and other bioelastomers) has been shown to be biocompatible both before and after cross-linking (4). As implants, such bioelastic polymers are biodegradable, leading to the release of products natural to the body, such as short peptide chains and free amino acids. These polymers, also referred to as elastomeric polypeptide biomaterials or simply bioelastic materials, can be prepared with widely different water compositions, with a wide range of hydrophobicities, with almost any desired shape and porosity, and with a variable degree of cross-linking (either chemically or by irradiation) by selecting different amino acids for the different positions of the monomeric units and by varying the cross-linking process used to form the final product.

The present invention arose in part with the realization that matrices prepared from these bioelastomeric materials can be used to hold a significant variety of drugs for diffusional release. Furthermore, residues with functional side chains, such as Glu, Ser, Lys, etc., can be used in order to attach drugs covalently. Then drug release could also be dependent on the rate of cleavage of the drug-polymer bond, depending on the particular type of bonding that is selected.

There are, however, additional capacities that these materials have which provide for site specificity and a special degree of control over the time release profile that is not available for materials previously used for the preparation of drug-containing compositions. These involves the capacity of these materials to be designed to function as free energy transducers, for example, specifically to exhibit thermomechanical transduction and chemomechanical transduction (mechanochemical coupling) (5). Associated with these transduction processes can be dramatic local swelling or contraction in aqueous media. Volume changes of an order of magnitude and more can be triggered to provide a greatly enhanced rate of drug release into the biological environment. Either swelling or contracting process can be used to trigger release of drugs in varying fashions as described herein.

Furthermore, bioelastomers can be prepared that contain "chemical clocks," a phrase used to refer to chemical processes that can be set to react upon the existence of a particular condition in contact with the bioelastic polymer for a preset length of time. For example, bioelastomers can be selected for triggering chemomechanical transduction in a constant external environment, such as would be experienced by a drug-impregnated implant, with the half-lives varying one-thousand fold from days to decades. Other bioelastomers can be designed so that a unit dose of drug present in the matrix is expelled immediately upon a change in conditions contacting the matrix, such as would occur when a particle prepared from a bioelastomer leaves the bloodstream and enters extracellular space in the vicinity of a tumor. Such materials are more in the nature of a bomb than a time-release system, since a change of contraction state (and resulting drug release) begins when the correct environment is contacted rather than occuring at a constant rate in a given environment, but the process governing them is basically the same. The half-life of the change in contraction state can likewise be selected to range from a few minutes to several hours or more.

A description of the process of designing bioelastomers specifically for use as "time-release systems" or "bombs," as these phrases relate to drug delivery systems, is described below in detail. Basically, a bioelastomer is selected that is capable of being chemically modulated upon contact with a pre-selected physiological condition so that the inverse temperature transition point of the bioelastomer changes; this change brings about unfolding and disassembly of polymer matrices or brings about a contraction that causes release of drug trapped in polymer matrices.

The specific examples used below to illustrate this process are mostly examples of elastomeric polypentapeptide matrices. However, it will be apparent that the same considerations can be applied to elastomeric tetrapeptide and nonapeptide matrices and to matrices prepared using these elastomeric units in combination with other polypeptide units as described previously for bioelastic materials.

Inverse Temperature Transition and Thermomechanical Transduction

The phenomena of inverse temperature transitions in aqueous systems is general and occurs in a number of amphiphilic systems, commonly polymers, that have an appropriate balance and arrangement of apolar and polar moieties. The polar species contribute to the solubility in water at low temperature, a solubility that results in waters of hydrophobic hydration for the apolar moieties. The waters of hydrophobic hydration, often referred to as clathrate or clathrate-like water, have specific thermodynamic properties: an exothermic heat of hydration (a negative $\Delta H$) and a negative entropy of hydration (6,7). On raising the temperature, by means of an endothermic transition (8), the low entropy waters of hydrophobic hydration become bulk water with a significant increase in solvent entropy as the polymers fold and aggregate, optimizing intra- and intermolecular contacts between hydrophobic (apolar) moieties with a somewhat lesser decrease in polymer entropy than increase in solvent entropy. Such polymers, when their transitions occur between 0° and 100° C., can be used to control events in the aqueous environments that occur in biology.

The polypentapeptide poly($Val^1$-$Pro^2$-$Gly^3$-$Val^4$-$Gly^5$), also written poly(VPGVG), is a particularly well-balanced polymer for biological utilities as its transition is just complete near 37° C. Below 25° C., it is miscible with water in all proportions where it exhibits a β-turn (see structural formula above) in which there occur hydrogen bonds between the $VAl^1$—CO and the $VAl^4$—NH moieties (9). On raising the temperature, the polypentapeptide folds into a loose helix in which the dominant interturn hydrophobic contacts involve the $Val^1$-$\gamma CH_3$ moieties in one turn and the $Pro^2$ $\beta CH_2$ moiety in the adjacent turn (10). The loose helical structure is called a dynamic β-spiral and is proposed to be the basis for the entropic elastomeric force exhibited by this material once cross-linked (11). Concomitant with the folding is an assembly of β-spirals to form a twisted filament which optimizes intermolecular contacts.

When poly(VPGVG) is cross-linked, for example, by 20 Mrads of γ-irradiation, an elastomeric matrix is formed which is swollen below 25° C. but which on raising the temperature through the transition contracts with the extrusion of sufficient water to decrease the volume to one-tenth and to decrease the length of a strip of matrix to 45% of its swollen length (2). This thermally driven contraction can be used to lift weights that are one thousand times the dry weight of the matrix. This is called thermomechanical transduction. As will be discussed below, any chemical means of reversibility or irreversibility shifting the temperature of the transition can be used, isothermally, to achieve chemomechanical transduction. Compositions of the invention are specifically selected to use this process to control the release of drugs from the composition.

Chemical Modulation of Inverse Temperature Transitions and Chemomechanical Transduction: Selection of Bioelastomers The temperature of inverse temperature transitions can be changed by changing the hydrophobicity of the polymer. For example, make the polypeptide more hydrophobic, as with poly($Ile^1$-$Pro^2$-$Gly^3$-$Val^4$-$Gly^5$), where replacing $Val^1$ by $Ile^1$ represents the addition of one $CH_2$ moiety per pentamer, and the temperature of the transition decreases by 20° C. from 30° C. for poly(VPGVG) to 10° C. for poly(IPGVG) (1). Similarly, decreasing the hydrophobicity as by replacing $Val^4$ by $Ala^4$, i.e., removing the two $CH_2$ moieties per pentamer, and the temperature of the transition is raised by some 40° C. to 70° C.

In terms of a generalized hydrophobicity scale, the COOH moiety is more hydrophobic than the $COO^-$ moiety such that by simply changing the pH of the environment contacting a bioelastomer with free carboxylate groups, the temperature of the transition can be changed. The transition temperature can be lowered by decreasing the pH and raised by increasing the pH when a carboxylate group is present (or other group capable of forming an ion upon increasing the pH). If an intermediate temperature is maintained, then a 20 Mrad cross-linked matrix of poly[4(VPGVG),(VPGEG)], that is, a random copolymer in which the two pentameric monomers are present in a 4:1 ratio, where E=Glu, will contract on lowering the pH and relax or swell on raising the pH (12). The temperature of the transition in phosphate buffered saline will shift some 50° C. from about 20° C. at low pH, giving COOH, to nearly 70° C. at neutral pH where all the carboxyls have been converted to carboxylate anions. See FIG. 1, panel A.

For similarly cross-linked poly[4(IPGVG),(IPGEG)], the temperature of the inverse temperature transition shifts from near 10° C. for COOH to over 50° C. for COO− (5). This shift is shown schematically in FIG. 1 (panel B). For this more hydrophobic polypentapeptide, which contains 4 Glu residues per 100 total amino acid residues, it takes twice as many carboxylate anions to shift the transition to 40° C. as for the less hydrophobic polypentapeptide based on the VPGVG monomer. Thus, it is possible to change the conditions of the transition by varying the hydrophobicity of the region surrounding the group that undergoes the chemical change. Since contraction and relaxation of the bulk polymer is dependent on the sum of all local thermodynamic states, sufficient control is possible merely by controlling the average environment of, for example, ionizable groups, such as by changing the percentage of monomers present in a random (or organized) copolymer.

When the pH is lowered (that is, on raising the chemical potential, $\mu$, of the protons present) at the isothermal condition of 37° C., these matrices can exert forces, f, sufficient to lift weights that are a thousand times their dry weight. This is chemomechanical transduction, also called mechanochemical coupling. The mechanism by which this occurs is called an hydration-mediated apolar-polar repulsion free energy and is characterized by the equation $(\delta\mu/\delta f)_n < 0$; that is, the change in chemical potential with respect to force at constant matrix composition is a negative quantity (13). Such matrices take up protons on stretching, i.e., stretching exposes more hydrophobic groups to water which makes the COO− moieties energetically less favored. This is quite distinct from the charge-charge repulsion mechanism for mechanochemical coupling of the type where $(\delta\mu/\delta f)_n > 0$ and where stretching of such matrices causes the release of protons. The hydration-mediated apolar-polar repulsion mechanism appears to be an order of magnitude more efficient in converting chemical work into mechanical work.

It may be emphasized here that any chemical means of changing the mean hydrophobicity of the polymer, such as an acid-base titrable function, dephosphorylation/phosphorylation, reduction/oxidation of a redox couple, etc., can be used to bring about contraction/relaxation. Most transitions will occur on the side chains of certain amino acids, preferably one of the 20 genetically encoded amino acids or a derivative thereof. Especially preferred are changes that can occur to genetically encoded amino acids as a result of contact with a physiological environment. Examples include ionization and neutralization of Glu, Asp, Lys, and His side chains; oxidation of the thio group of Cys (for example to form cystine) or reduction of an oxidized form to Cys; amidation of Glu or Asp; and deamidation of Gln or Asn. It is also possible to attach a moiety containing a functional group that undergoes a transition under conditions different from those attainable for naturally occurring amino acid side chains. For example, a sulfate ester of Ser can be prepared in which sulfate ionizations will occur at a pH outside the range experienced by carboxylate groups. A change in the oxidation state of NAD, a flavin, or a quinone attached to an amino acid by reaction of a functional group in the modifying moiety and a functional group in an amino acid side chain is also effective. A specific example of such a modified amino acid residue is a riboflavin attached to the carboxylate group of a Glu or Asp residue through formation of an ester linkage. Another example would be a heme moiety covalently bonded to the side chain of an amino acid. For example, protoporphyin IX can be attached to the amino group of Lys through one of its own carboxylate groups. Heme A (from the cytochromes of class A) could be attached in a similar manner. Change in the oxidation state of, or coordination of a ligand with, the iron atom in a heme attached to an amino acid side chain can also be used to trigger the desired transition.

It is also possible to exert fine control over the transition from a relaxed to a contracted state (or vice versa) by controlling the average environment in which the various functional groups undergoing transition are located. For example, the hydrophobicity of the overall polymer (and therefore the average hydrophobicity of functional groups present in the polymer) can be modified by changing the ratio of different types of monomeric unit, as previously exemplified. These can be monomeric units containing the functional group undergoing the transition or other monomeric units present in the polymer. For example, if the basic monomeric unit is VPGVG and the unit undergoing transition is VPGKG, where K is a lysine residue, either the ratio of VPGVG unit to VPGKG units can be varied or a different structural unit, such as IPGVG, can be included in varied amounts until the appropriate transitions temperature is achieved.

In general, selection of the sequence of amino acids in a particular monomeric unit and selection of the required proportion of monomeric units can be accomplished by an empirical process that begins with determining (or looking up) the properties of known bioelastomers, making similar but different bioelastomers using the guidance provided in this specification, and measuring the transition temperature as described herein and in the cited patents and patent applications. Preferably, however, one uses tables of relative hydrophobicity of amino acid residues (either naturally occurring or modified) to compute the transition temperature without experimentation. For example, see Y. Nozaki and C. Tanford, *J. Biol. Chem.* (1971) 246:2211–2217, or H. B. Bull and K. Breese, *Archives Biochem. Biophys.* (1974) 161:665–670, for particularly useful compilations of hydrophobicity data. Some 30 different hydrophobicity scales exist, with the hydrophobicity scales that show tryptophan (Trp) as the most hydrophobic (or at least one of the most hydrophobic) residues being more appropriate for the practice of the present invention. For example, a rough estimate can be obtained of the likely transition temperature by summing the mean hydrophobicities of the individual amino acid residues in the monomeric units of the polymer and comparing the result to the sum obtained for polymers having known transition temperatures.

More accurate values can be calculated for any given polymer by measuring transition temperatures for a series of related polymers in which only one component is varied. For example, polymers that mostly contain VPGVG monomers with varying amounts of VPGKG monomers (e.g., 2%, 4%, and 8% K) can be prepared and tested for transition temperatures. The test merely consists of preparing the polymer in uncrosslinked form, dissolving the polymer in water, and raising the temperature of the solution until turbidity appears, which indicates the precipitation of polymer from solution. If the transition temperatures are plotted versus the fraction of VPGKG monomer in the polymer, a straight line is obtained, and the fraction of VPGKG necessary for any other desired temperature (within the limits indicated by 0% to 100% of the VPGKG monomer) can be obtained directly from the graph. When this technique is combined with the rough estimating ability of hydrophobicity summing as described above, any desired transition temperature in the range of liquid water can be obtained.

Chemical Clocks for Controlling Rates of Drug Release

For biodegradable drug delivery systems, whether degradation occurs by enzymatic or by salt-catalyzed hydrolytic cleavage, control of hydration becomes the key to rate of degradation. When beginning with drug-doped condensed matrices, therefore, controlling the extent and location of hydration (solvent swelling) is a key to drug release whether by diffusion, by release of entrapment or by cleavage of a drug-polymer bond.

It is possible to have polymer matrices that are so dense and hydrophobic as to render them essentially non-biodegradable. This is even possible with polypeptide matrices, as has been shown with poly(Glu-co-Leu), where 1:1 copolymer was recovered intact after 15 months in vivo (14). Nonetheless, treatment with dilute NaOH and neutralizing to pH7 resulted in complete biodegradation. Presumably, based on the information developed by the present inventor, the dilute base treatment was sufficient to result in the formation of interfacial COO$^-$ moieties which could start the swelling process required for degradation. However, no control mechanism was known for that system to allow preselection of different degradation rates or conditions.

The already described polypeptide matrices capable of exhibiting inverse temperature transitions, such as poly(VPGVG), poly(IPGVG), poly(VPAVG), poly(VPGG), poly(VAPGVG), poly(VPGFGVGAG), etc., where A=Ala and F=Phe, with water contents ranging from less that 10% to greater than 90% (1, 17–19), can be used in the practice of the present invention without modification. Each of these material has a specific rate of degradation in different physiological situations and can be used as a drug-impregnated matrix for any use needing that degradation rate. Furthermore, the rate of degradation of such matrices in vivo can be varied from exhibiting half-lives of days to decades by modifications of the polymers as described herein.

What is desired in providing control of drug release is an adequately responsive polymer coupled to a chemical clock with a broad range of selectable half-lives that would provide the trigger for swelling. Polymers that exhibit chemically modulable inverse temperature transitions are an ideal material for such drug delivery matrices, and bioelastic materials (elastomeric polypeptide biomaterials) form just such matrices.

Bioelastomeric material provide a chemically modulable polymer system as part of which there can be a controlled rate of presentation of more polar species such as the carboxylate anion. By the mechanism described above where $(\delta\mu/\delta f)_n < 0$, the pKa of a carboxyl moiety in a polymeric chain can be increased by increasingly vicinal hydrophobicity (13,15).

Asparagine (Asn) and glutamine (Gln) residues in a bioelastic monomer can function as one type of chemical clock that will control the swelling (and therefore degradation) rate of a dense, drug-containing polymer. More than sixty pentameric sequences in which the central residue is Asn or Gln are known; at 37° C. in phosphate buffered saline pH 7.5 and ionic strength 0.15, the half-lives of the carboxamide side chains varies from six days for Gly-Ser-Asn-His-Gly to 3409 days for Gly-Thr-Gln-Ala-Gly with Gly-Ile-Asn-Ala-Gly having an intermediate half-life of 507 days (16). More hydrophobic residues will slow the decay further.

While not necessarily water soluble as the free pentamers, the more hydrophobic carboxamide-containing pentamers could be part of larger polypeptides. While a range for the half-lives of a factor of 500 was demonstrated, with greater hydrophobicity in the primary structure contributing to increased half-lifes and lesser hydrophobicity contributing to decreased half-lifes and with polypeptide folding (tertiary structure) also contributing, it is possible to vary the half-lifes of drug-containing bioelastomeric matrices from days or fractions of days to decades.

Interfacial hydrolytic cleavage of a carboxamide to carboxylate anion with resultant local swelling will lead to polymer degradation. The trigger of interfacial carboxamide hydrolytic cleavage can be preprogrammed by the sequence of the polypeptide, and by more general polypeptide hydrophobicity, to occur at a given rate. The occurrence of this control step has the consequence of local swelling (over a distance of a few angstroms for an individual chemical change). The second control step over rate of drug release would be the rate of degradation of the polypeptide involved in the local swelling, which can also be enhanced by having esters in the backbone (i.e., depsipeptides). The rate of hydrolytic cleavage of the backbone ester would depend on the hydrophobicity of residues in the sequence most proximal to the ester residue as well as on vicinal hydrophobicity contributed by folding. A third control step could be having the drug bound to the polypeptide through side chains by bonds that would also have different rates of cleavage. Thus, preprogramming of drug release, by release from entrapment, by controlled swelling and subsequent degradation, and/or by subsequent hydrolytic cleavage of the polymer-drug bond, becomes possible when using matrices which undergo chemically modulable inverse temperature transitions.

The rate of carboxamide/carboxylate anion conversion is the initial and most significant control step for drug release but additional control steps are possible such as introducing esters into the polypeptide backbone. The proximity of the backbone ester to hydrophobic moieties will affect its rate of hydrolytic cleavage further opening access to the eroding surface. Also, the drug may be covalently attached to the polymer and the rate of this bond cleavage could also affect the rate of drug release. Of course, the drug could simply be trapped within the matrix with release occurring by diffusion on swelling and/or on backbone degradation.

Whether drug release is by controlled swelling with enhanced rate of degradation or by contraction with expelling of contents (described below), the devices can be designed with the specificity based on a unique chemical aspect of the target site much as proteins themselves are brought to fold or unfold, to assemble or disassemble and to function with highly cooperative response profiles and to do so at specific sites.

Drugs Useful in the Practice of the Invention

Little attention has been paid so far in this discussion to the drug that will be present in or attached to the biopolymeric matrices. In fact, there are no known limits of the structure of drugs that can be used in compositions of the present invention. Accordingly, the word "drug" as used herein means any substance, whether of chemical or biochemical origin, that causes a physiological effect in a biological system. Examples of physiological effects include death (antibiotics and toxins), blood clotting (coumarin), cell growth (platelet derived growth factor), analgesia (aspirin), and modification of pH (magnesium or calcium hydroxide). Drugs of any structure can be impregnated into a contracted bioelastomeric matrix and then released as the matrix swells and degrades or impregnated into a swollen matrix and expelled by a contraction of the matrix (discussed in more detail below). Since in either of these processes the matrix acts essentially as a sponge, the structure of the drug is of little interest. Simple ions, such as lithium, can be impregnated in the matrix, but the matrix in penetrated by ions only with difficulty, so that a better tactic for ions is to capture the ions in a liquid inside a membrane made of a bioelastomer. A bioelastic membrane enclosing a liquid-filled space that contains a dissolved or suspended drug is not dependant on the structure of the drug, so that this type of structure can be used for any type of drug. Contraction of the membrane will expell the liquid through pores in the membrane or by membrane rupture.

Larger drugs, whose diffusion out of the matrix is inhibited, are preferred candidates for use with the embodiment of the present invention in which a drug is entrapped in the matrix. Preferred drugs for this embodiment have molecular weights of at least 200, more preferably at least 500. Since the size of pores in the matrix can be varied by controlling the degree of crosslinking of the bioelastomer (more crosslinking leading to smaller pores), considerable variation in size is possible, up to and including large molecules of biochemical origin, such as antibodies and other proteins. Accordingly, the upper limit of preferred molecular weights is about 1,000,000, with more preferred drugs having molecular weights of less than about 500,000, most preferably less than 250,000. Drugs trapped in the matrix can be non-polar, polar, or charged, without affecting their ability to be used in a drug delivery system of the invention.

One class of drugs particulary preferred for use with bioelastic matrices are drugs based on polypeptides. These can be small molecules, such as antibiotics of the polypeptide class or chemotactic hexamers or nonamers of the types described in U.S. Pat. No. 4,693,718 (hexamers) or U.S. Ser. No. 184,147, filed Apr. 21, 1988, (nonomers; now U.S. Pat. No. 4,976,734 or large proteins, such as antibodies or bioactive molecules such as erythropoietin.

Other examples of specific drugs that can be used with this aspect of the invention include oxytocin, vasopressin, angiotensin, rennin, polymyxin, erythromycin, and coumarin.

As an example of a bioelastic matrix loaded with a trapped (i.e., non-covalently attached) drug, see the Examples section of this specification. The chemotactic hexapeptide VGVAPG and the chemotactic nonapeptide GFGVGAGVP were loaded into a bioelastic matrix simply by lowering the temperature of a suspension containing a bioelastomer until the bioelastomer was in its swollen state. Chemotactic peptide was then added at various concentrations and the temperature of the suspension was raised until the bioelastomer switched to its contracted state. In each case, some of the chemotactic material became trapped in the contracted matrix, the amount depending on the concentration of the chemotactic material in the original suspension. Other substance can be impregnated in a matrix of the invention in the same manner.

Optionally, drugs can be attached to the polymeric backbone of the matrix by providing a covalent bond between a functional group on the drug and a functional group on a side chain amino acid of the polymer. Techniques for attaching biologically active compounds (i.e., drugs) to functional groups on various types of surfaces are well developed in the art and need not be described here in detail. As examples of known techniques for attaching biologically active molecules to surfaces, see PCT Publication No. 8911271 (Nov. 30, 1989; attaching lipids to a polymer), EPO Publication No. 339821 (Nov. 2, 1989; attaching biologically active materials to surfaces via bifunctional reagents), EPO Publication No. 338173 (Oct. 30, 1989; use of ionic binding sites to join active molecules to a substrate), and PCT Publication No. 8908130 (Sep. 8, 1989; attaching two proteins to each other).

Preferred drugs for covalent attachment include those having functional groups that allow easy attachment to the matrix. Such functional groups can be present as part of the molecule commonly thought of as the drug, or a compound known to operate as a drug can be modified to include a functional group that is used for attachment, where the new molecule containing the functional group also exhibits biological active (although it may be of a different, usually lesser, degree). Any loss of activity, however, will generally be offset by presentation of the drug in a composition that more accurately controlls presentation of the drug to various environments in the body being treated.

Examples of suitable attachments include those in which the drug is attached to the polymer as a result of a chemical reaction between a functional group in the drug and a functional group in a side chain of an amino acid residue in the polymer. For example, the functional group in the drug can be an amino group and the functional group in the matrix can be a carboxylate group; alternatively, the first (i.e., drug) functional group can be a carboxylate group and said second (i.e., matrix) functional group can be a hydroxyl, amino, or thiol group; the first functional group can be a thiol group and the second functional group can be a thiol or carboxylate group; or the first functional group can be a hydroxyl group and the second functional group can be a carboxylate group. Additionally, various bifunctional linking groups, such as diacids (e.g., succinic acid or glutamic acid), diamines (e.g., 1,4-diaminobutane), diones (e.g., glyoxal), amino acids (e.g., lysine), and hydroxyamines (e.g., 2-aminoethanol), can be used to link the two functional groups.

Drug Delivery Using Materials Capable of Mechanochemical Coupling: Selected Examples Given the number of ways that contraction and relaxation (swelling) can be chemically achieved, there are innumerable delivery constructs that may be used based on a chemically induced shift from one such state to the other. In this specification, such shifts will be referred to a changes in the contraction state of the bioelastomer, although they could equally well be referred to as changes in the relaxation state. Three systems that rely on such a change of contraction state are discussed here in detail:

(1) monoliths with preprogrammed chemical clocks where drug release is brought about by chemically triggered relaxation (swelling);

(2) chemomechanical pumps where drug release is achieved by chemically driven contraction, as in the expulsion of the contents of an elastic envelope or as in the wringing out of a sponge; and (3) nanospheres that may be site-targeted by size and also by chemical triggering.

In the latter two examples, site-targeting could be achieved by a relatively small difference in a chemical property such as pH. For pH, this can occur due to hydrophobicity-induced pK shifts and the cooperativity of the charging process involved in chemomechanical coupling (13, 15). Other mechanisms also exist, as discussed herein.

Carboxmide Chemical Clocks for Controlling Rate of Surface Swelling Followed by Degradation of Doped Monolith: This is accomplished by preparing an non-degradable, contracted-state matrix containing a uniform distribution of drug (either impregnated in the matrix or covalently attached). Degradation of a slab monolith can occur once sufficient hydration is achieved, and sufficient hydration of the relatively hydrophobic matrix can occur once the temperature of the inverse temperature transition is raised above 37° C. by chemical perturbation. The rate-limiting chemical perturbation in such a system is the rate at which a spontaneous reaction, such as hydrolysis, occurs at the aqueous milieu-slab interface.

An example of a chemical trigger involving hydrolysis is the inclusion of asparagine (Asn) or glutamine (Gln) within the polymer sequence. The rate at which the carboxamide to carboxylate anion chemical perturbation occurs can be controlled by the hydrophobicity of adjacent residues and the folding of the remainder of the polymer chain. By properly choosing the adjacent residues and hydrophobicity of the matrix in general, the half-life for the hydrolysis can be altered from days to decades, as has been previously described.

Figure 2:
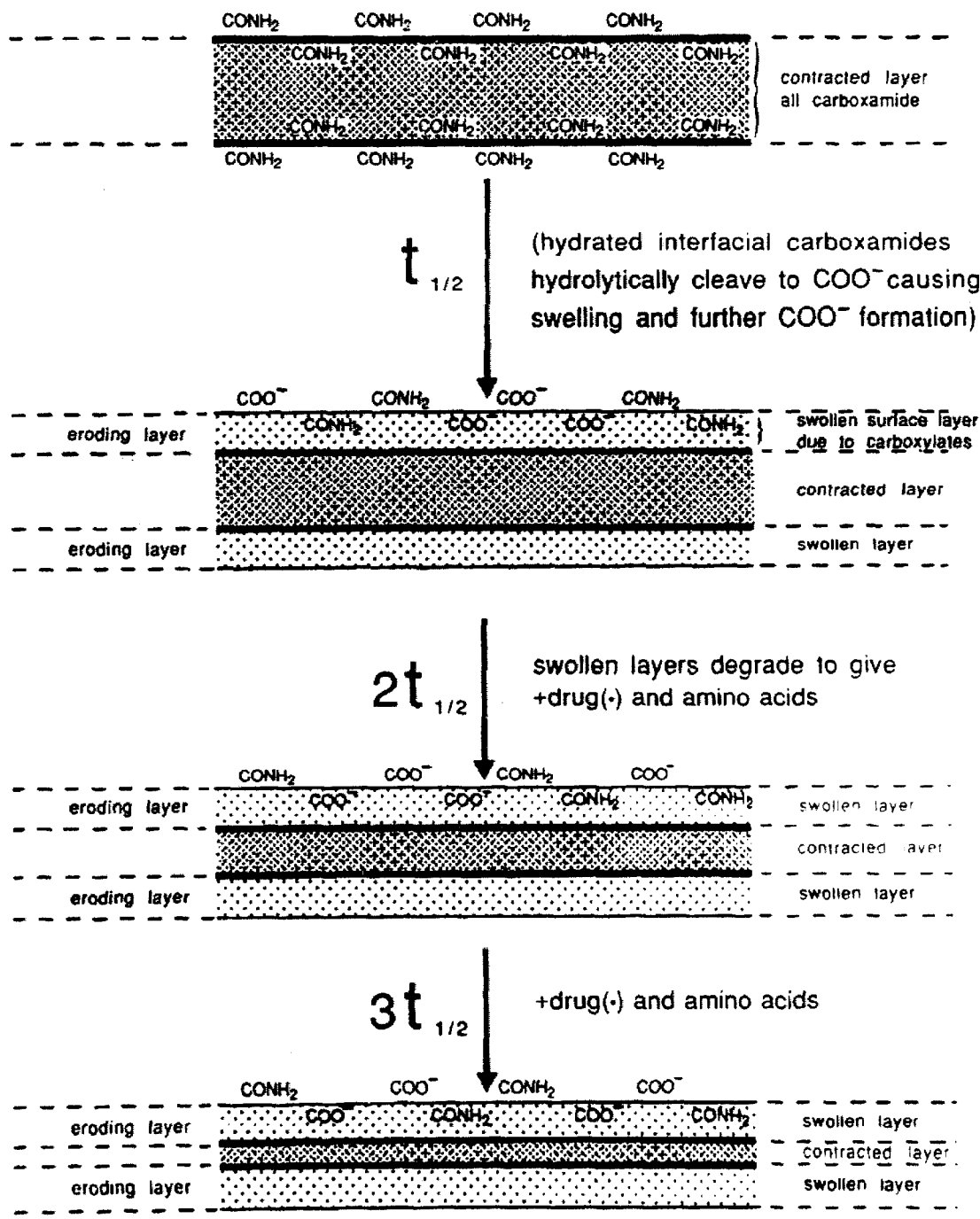
FIG. 2 is a diagram showing degradation of a monolithic composition of the present invention uniformly doped with drug which swells at a rate determined by hydrolysis of functional groups present in the polymer portion of the composition.

As depicted in FIG. 2 and demonstrated in FIG. 1, once a carboxylate anion is formed, it shifts the temperature for the swelling transition for the chains, within some few tens of Angstroms of the ion, from below to above body temperature. This will cause a surface layer to swell at a rate dependent upon the $CONH_2$ to $COO^-$ transition. As the surface layer swells, the drug is released either by diffusion or, if covalently bonded to the polymer, by subsequent polymer backbone cleavage and/or polymer-drug bond cleavage. The rates of these latter cleavages can be sufficiently slow as to contribute to the overall rate of drug release or they can be faster than the $CONH_2$ to $COO^-$ transition such that the deamidation step would be rate limiting, in accordance with the desires of the user. As the surface layer swells and sufficient water and salts can approach new carboxamides, they can also undergo cleavage with their characteristic rates. The process continues until the slab is degraded.

It should also be appreciated that the chemical clock can be the drug-polymer bond itself (for example, an ester or amide bond to a Glu, Asp, or Lys residue) within the matrix with an appropriately altered vicinal hydrophobicity to control rate of hydrolytic or enzymatic cleavage.

Figure 3:
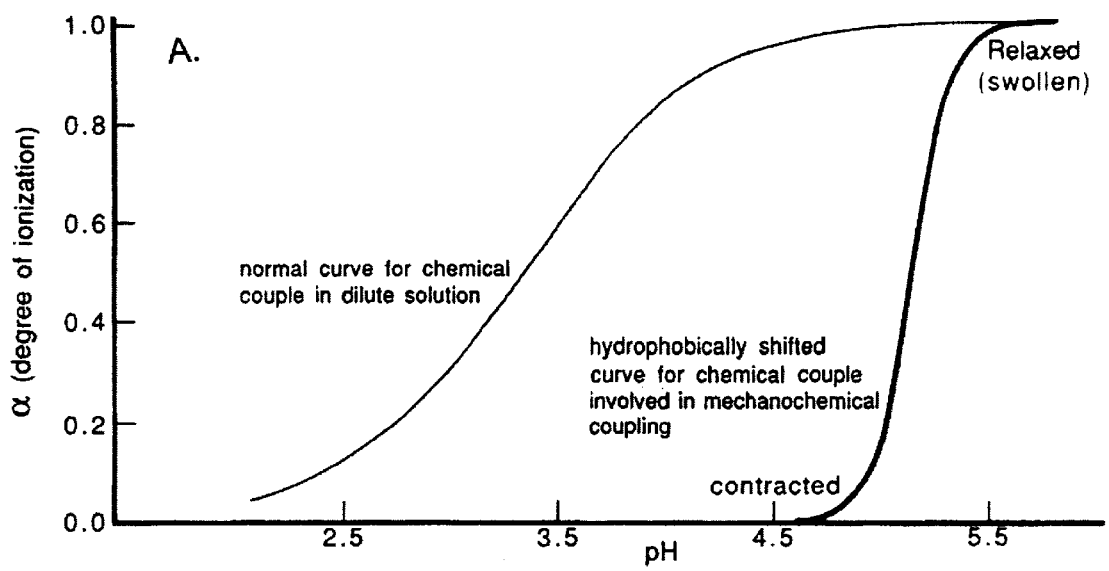
FIG. 3 is a graph showing cooperativity and pK shifts for both anionic and cationic chemical couples and the effects of such shifts on the relaxed (swollen) or contracted state of a bioelastomeric polymer.
Figure 3:
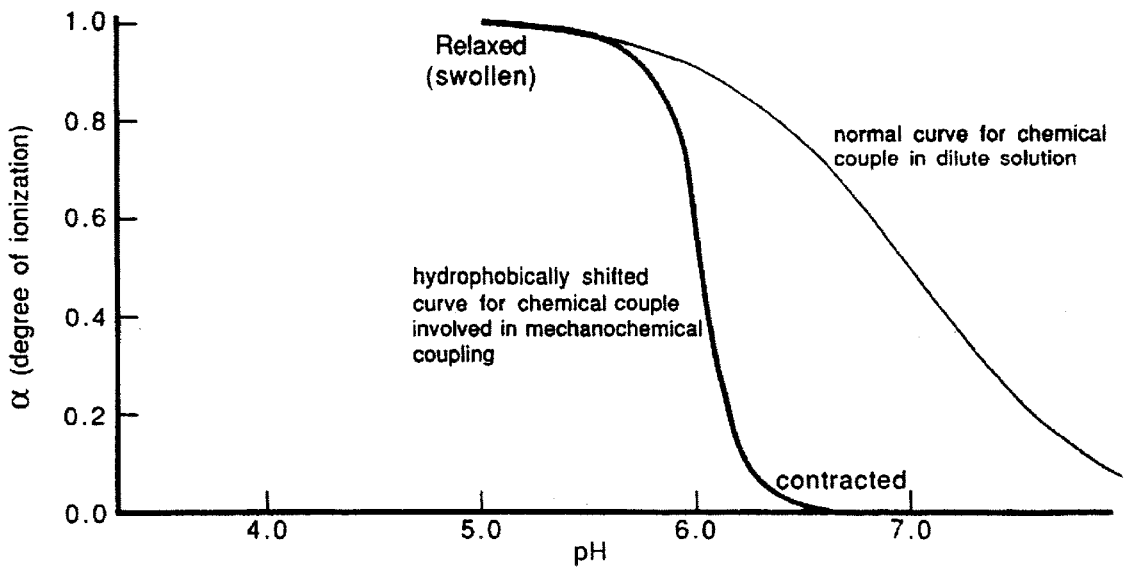

Hydrophobicity Induced pKa Shifts and Cooperativity for Ionization In Matrices Capable of Chemomechanical Coupling: At the molecular level, the mechanism for mechanochemical coupling is considered in water- and structure-limited systems to arise out of the competition of the apolar (hydrophobic) and polar species for hydration. As the hydrophobic moiety with its waters of hydration becomes too proximal to a polar species with its hydration shell, the interceding water molecules cannot simultaneously provide for the free energies of hydration of both the apolar and polar species with the result of an unfavorable increase in free energy. This has profound effects on an ionizable polar species such as the COOH/COO— couple. With the cross-linked matrix of poly[4(VPGVG),(VPGEG)], at low pH the matrix is contracted. Even though the relatively hydrophobic matrix when contracted is more than 50% water by weight, the system is water-limited. As the pH is raised, the ionization of the COOH is delayed because of inadequate waters of hydration for the COO— moiety. This leads to an increase in the pKa in proportion to the hydrophobicity of the matrix (13,15). As the first few COO— moieties do appear, they cause the matrix to swell making it easier for subsequent anions to form. There is therefore a cooperative effect, and the titration curve becomes steeper as shown in panel A of FIG. 3. If the titrable group is a cationic chemical couple as —$NH_3^+$/$NH_2$ or as the His+/His (imidazolium/imidazole) couple, the free energy of the more polar species is again most significantly raised. The result is a pKa that is lowered and again a cooperative effect is observed as depicted in panel B of FIG. 3. The cooperative effect, apparent as the steepened pH dependence for the degree of ionization and for the mechanochemical coupling, means that a site with a more acidic pH could either selectively cause a contraction (for an anionic chemical couple) or a swelling (for a cationic chemical couple) of a matrix capable of exhibiting chemical modulation of an inverse temperature transition.

Compositions useful for this embodiment can be prepared as previously described when the drug is impregnated in the matrix without covalent attachment; namely by swelling a normally contracted (at the operating temperature) matrix in a solution or suspension of the drug at a low temperature and then raising the temperature of the solution until the matrix contracts, trapping the drug in the pores of the matrix. The matrix itself can be prepared in any of the manners previously described; see any of the U.S. patents previously cited. When the drug is covalently attached to the matrix, several attachment procedures are possible. For example, the drug can be attached to an amino acid and the drug-modified amino acid used in the synthesis of the monomeric units from which the polymer is made. Alternatively, the drug can be attached to a functional group in the side chain of the matrix after the matrix is formed, attached to a terminus of the polymer chain, or attached randomly to the chain throught the use of a highly reactive function group. All of these techniques for modifying bioelastomers (for other purposes) are described in earlier patents and patent application.

Figure 4:
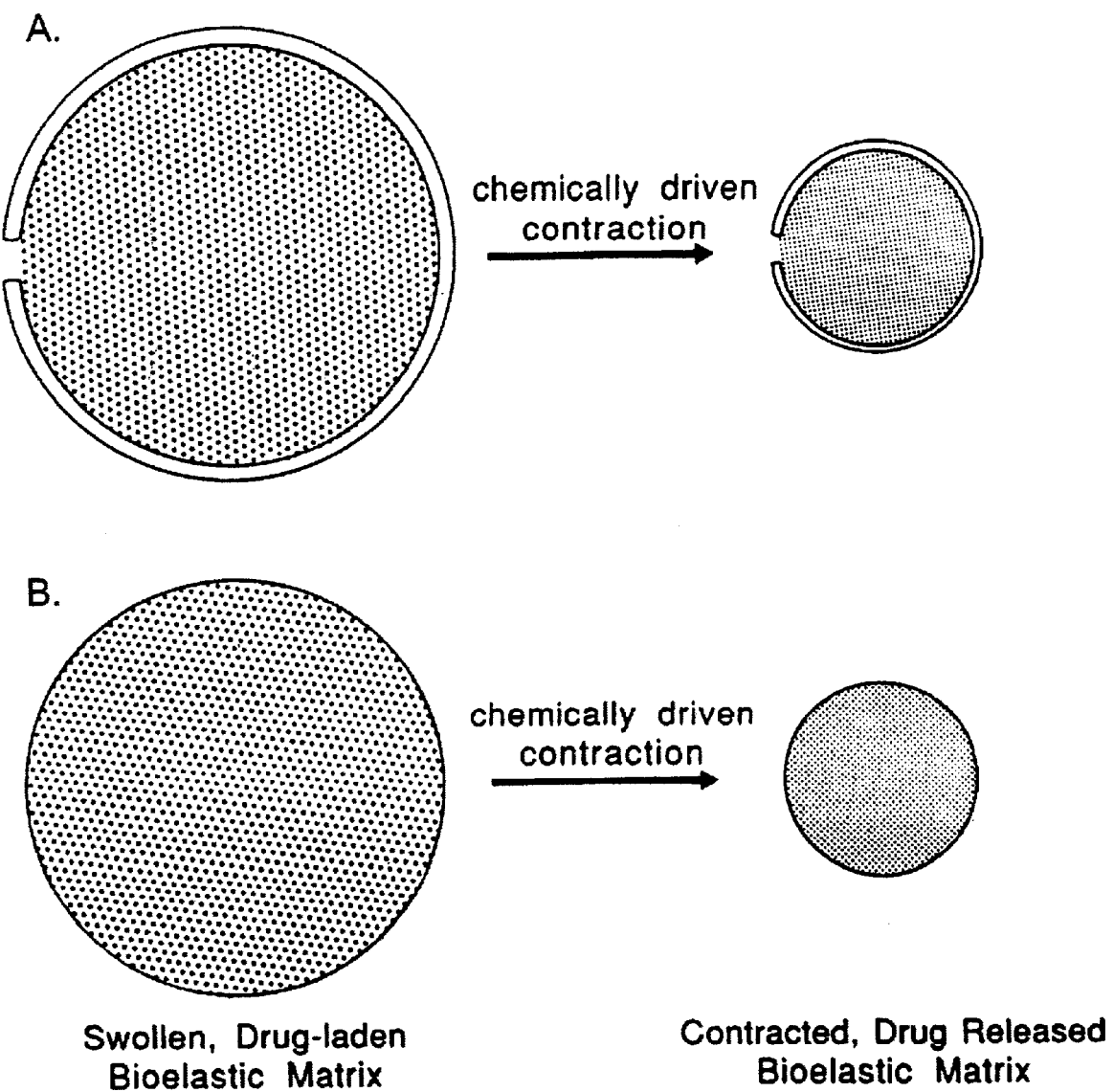
FIG. 4 is a diagram showing two types of chemomechanical pumps: a swollen, drug-laden bioelastic matrix that is chemically driven to contraction and expulsion of drug upon contacting a preselected physiological condition and a liquid-filled bioelastic envelope that expels its liquid contents (which contain the drug) upon contacting the preselected condition.

Chemomechanical Pumps: Two constructs for chemomechanical pumps may be considered, one where a chemomechanical membrane surrounds the drug as shown in panel A of FIG. 4 and the other a monolith which on contraction much as a sponge delivers its drug (panel B). Both of these constructs provide site specific release of drug, whenever a site has a sufficiently distinct chemical property. A unique property of a site can be a pH other than the usual extracellular pH; it can be an increased enzyme activity; it can be the increased concentration of either component of a redox couple; it could be an enhanced oxidative capacity with excess superoxide, hydrogen peroxide or hypochlorite, etc.; or it could even be a different salt concentration (20). Also, rather than a contractile release, a degradational release could be achieved by a site specific chemical signal resulting in swelling and enhanced degradational release as considered for the chemical clock except that the stimulus of the site to which the composition is transported would provide the stimulus rather than the preprogrammed chemical clocks acting in a single location.

Each of these constructs is easily prepared. Preparation of a sponge-like construct has already been discussed. However, instead of selecting a bioelastomer that is in the contrasted state at body temperature, as is desired for an implant that will release drug by swelling and degrading, for this embodiment a bioelastomer is selected that will remain in the relaxed state until an appropriate chemical or other environmental condition is achieved, such as a change in pH on passing from the stomach to the small intestine. Contraction of the matrix upon contact with the appropriate environment expells the drug impregnated in the matrix.

Envelope-like embodiments can be prepared in much the same manner as liposomes and other membrane-encased liquids, typically by subjecting a suspension of the membrane-forming material in a solution or suspension of the drug to high shear forces. It is also possible to manufacture capsules in a variety of sizes and with appropriate pores as desired using standard manufacturing techniques for capsules, because as the bioelastomers described herein lend themselves to such manufacturing processes.

Nanospheres: Particles of different radii can be produced by cross-linking particles formed during the stage of nucleation and accretion that occurs just before the inverse temperature transition. At this stage, particle diameters from 10 to 1000 nm have been observed (21,22), and particles of other sizes can be prepared by manipulation of the solution of bioelastomer (such as by allowing accretion to proceed or by subjecting the solution to high shear forces). The particles can be cross-linked by any of a number of ways including γ-irradiation, and they can have drugs attached or impregnated therein. Accordingly, sites differentially reachable by particle size can be sites for selective drug delivery, and size specificity can readily be coupled to chemical specificity as noted above.

One example of such a system, in which differential drug distribution is based on particle size alone, is the proposed use of particles of a size selected to be excluded by the vascular bed of normal tissue but which can pass into the vascular bed of tumors, which have been reported to pass larger particles. Such particles are generally about 0.1 micron in diameter. When particles of an appropriate size to achieve this selective distribution also are selected so that they release their drug contents only if an appropriate chemical trigger is present (such as a pH more acidic than that found in normal tissue, a common property of tumors), then a doubly selective drug delivery system is provided, which can allow for the use of highly cytotoxic substance for cancer control while minimizing the release of the toxins in inappropriate locations.

The invention now being generally described, the same will be better understood by reference to the following examples, which are provided for purposes of illustration only and are not to be considered limiting of the invention unless so specified.

EXAMPLE
Induction of Fibroblast Migration Using Bioelastomers Impregnated with Chemotactic Polypeptides Chemotaxis assays were run to determine the concentration of diffusible hexapeptide and nonapeptide chemotactic peptides most suitable for impregnation in a crosslinked polyhexapentapeptide/polynonapentapeptide matrix intended for use in tissue reconstruction. The chemotactic hexapeptide is described in U.S. Pat. No. 4,605,413. The chemotactic nonapeptide is described in U.S. Pat. No. 4,693, 718. Formation of the matrix is described in detail in U.S. Pat. No. 4,870,055. This is a matrix that does not contain chemically modifiable groups and therefore does not fall within the scope of the present invention. However, the Example shows how drugs can be impregnated into a bioelastic matrix and how the amount of drug contained in the matrix can be varied to achieve a desired biological effect.

The initially insoluble (at room temperature) matrix was swollen at 5 C. in solutions of different concentrations of the monomers, taken to 37° C. (above the transition temperature; therefore in a contracted state), and used in the migration experiment. The fibroblast migration experiment is described in U.S. Pat. No. 4,693,718.

Figure 5:
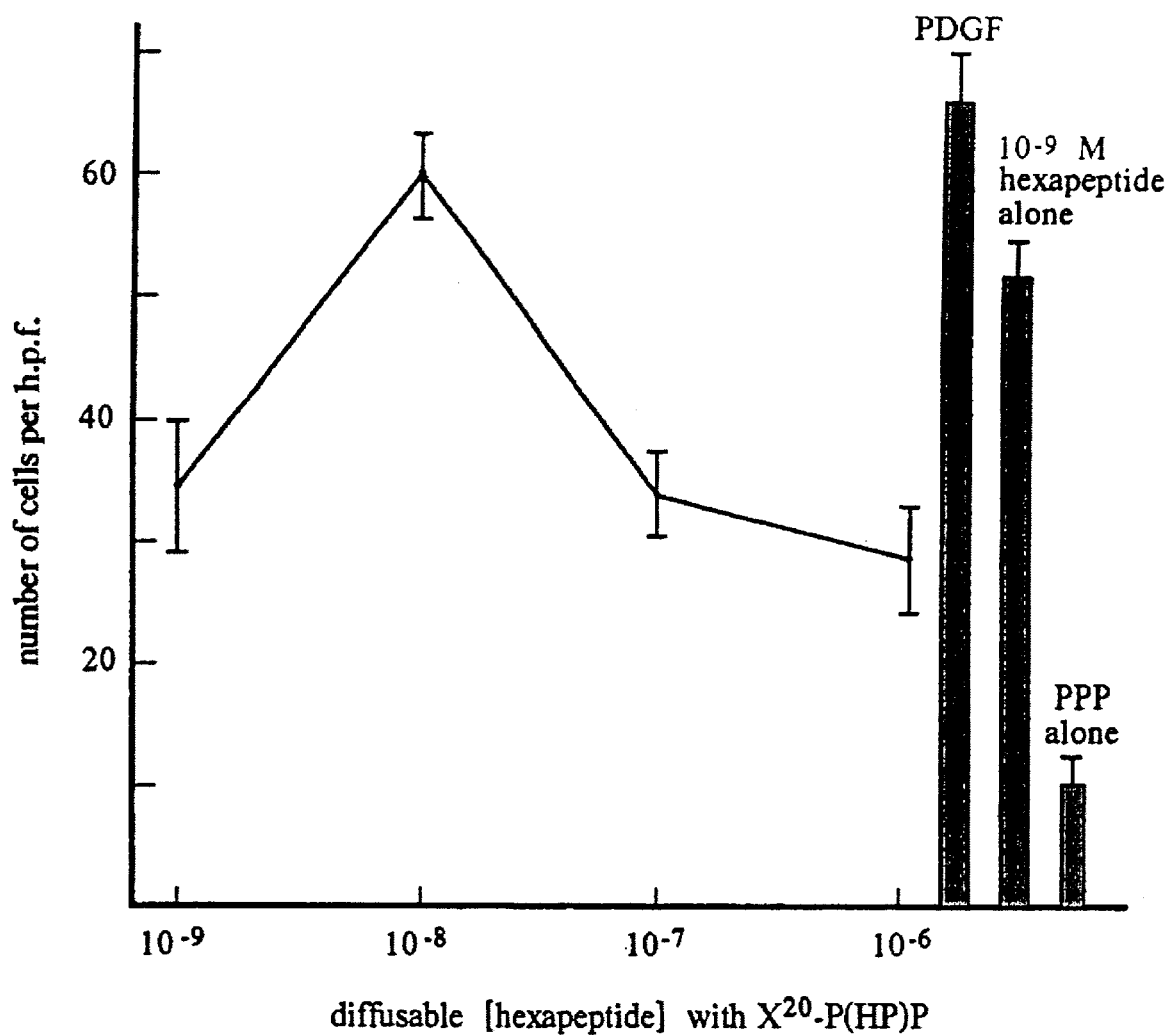
FIG. 5 is a graph showing fibroblast migration induced by release of a chemotactic hexapeptide from a bioelastomeric matrix.

FIG. 5 gives the data for the 20 MRAD-crosslinked elastomeric polyhexapentapeptide doped with various concentrations of the chemotactic hexapeptide. The peak of activity was at an impregnation concentration of $10^{-8}$ M, and consequently a series of implants designed for tissue reconstruction (see U.S. application Ser. No. 184,873, filed Apr. 22, 1988, now U.S. Pat. No. 5,336,256, for a description of the implant) was prepared with this concentration. As shown in FIG. 5, the positive control (platelet-derived growth factor; PDGF) showed good response with a net migration of 65 cells per high power (40×) field (hpf). Polypentapeptide alone showed some directed migration, 10 cells per hpf, but this is almost at background level and is not significant. Hexapeptide alone at $10^{-9}$ M and hexapeptide at $10^{-9}$ M plus polypentapeptide (PPP) elicited positive responses, a significant finding indicating that the insoluble polyhexapentapeptide matrix is not inhibiting the chemotactic activity of the hexapeptide. There is interaction between the polyhexapentapeptide matrix and the hexapeptide, though, because the peak of activity for hexapeptide alone is $10^{-9}$ M.

Figure 6:
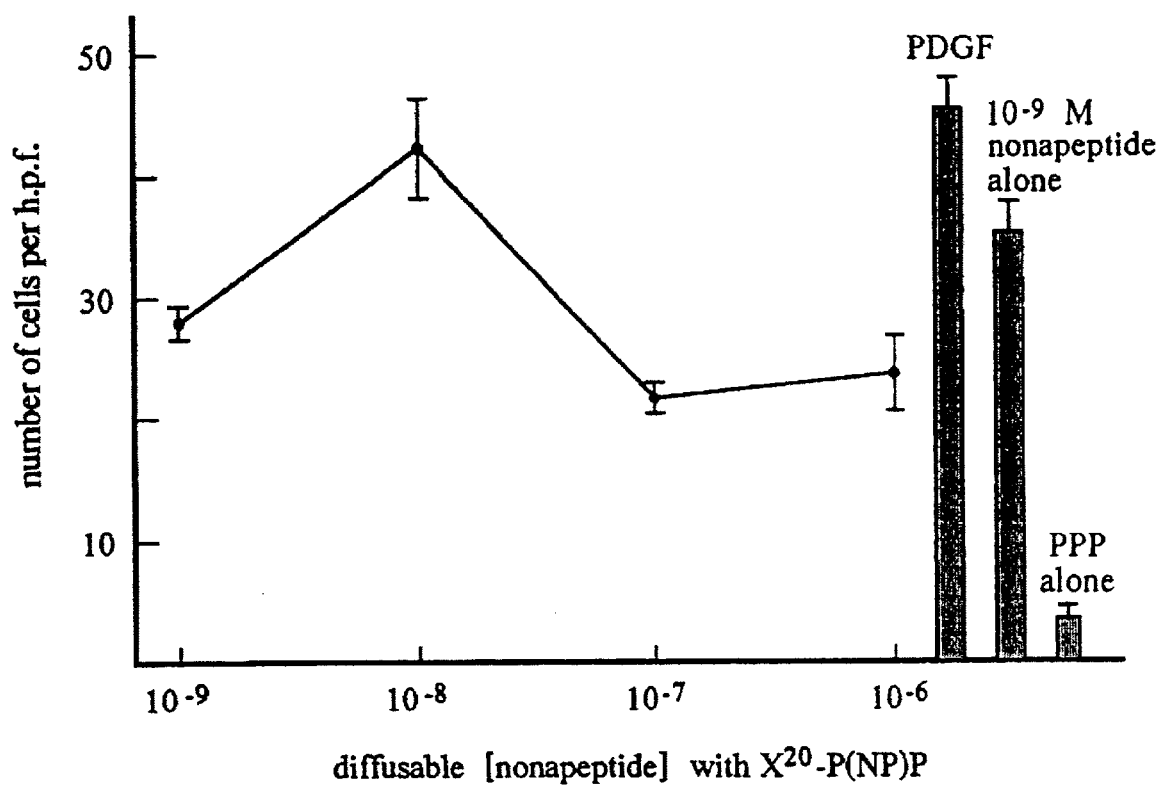
FIG. 6 is a graph showing fibroblast migration induced by release of a chemotactic nonapeptide from a bioelastomeric matrix.

FIG. 6 shows the data for the polynonapentapeptide and the nonapeptide. The same observations pertaining to FIG. 5 also apply to FIG. 6; i.e., good positive response, low PPP-elicited background migration, and similar response between nonapeptide alone and with PPP. The concentration curve for the nonapeptide alone (data not shown) peaked at $10^{-9}$ M.

All publications and patent applications mentioned in this specification are herein incorporated by reference to the same extent as if each individual publication or patent application was specifically and individually indicated to be incorporated by reference at the location where cited.

The invention now being fully described, it will be apparent to one of ordinary skill in the art that many changes and modifications can be made thereto without departing from the spirit or scope of the appended claims.

What is claimed is:

1. A drug delivery composition capable of selective release of said drug into a preselected physiological environment, comprising:

(1) a synthetic bioelastic polypetide polymer comprising repeating elastomeric units selected from the group consisting of bioelastic pentapeptides, tetrapeptides, and nonapeptides, wherein said repeating units comprise amino acid residues selected from the group consisting of hydrophobic amino acid and glycine residues and wherein said repeating units exit in a conformation having a β-turn; and (2) a drug retained by said polymer;

wherein said polymer is selected to be in a first contraction state, selected from the group consisting of contracted and relaxed bioelastomer states, when contacted with a physiological environment present in a human or animal to whom said composition is administered and wherein said polymer contains a reactive functional group that undergoes a reaction, either in the presence of said physiological environment or when said polymer is transported by a natural process in said human or animal to a location having a different physiological environment, to produce a second functional group, wherein the presence of said second functional group in said polymer causes said polymer to switch to the other of said contraction sites, thereby making said drug available for release from said composition into said preselected physiological environment.

2. A drug delivery composition capable of selective release of said drug into a preselected physiological environment, comprising:

(1) a synthetic bioelastic polypeptide polymer comprising repeating elastomeric units selected from the group consisting of bioelastic pentapeptides, tetrapeptides, and nonapeptides, wherein said repeating units comprise amino acid residues selected from the group consisting of hydrophobic amino acid and glycine residues and wherein said repeating units exist in a conformation having a β-turn; and (2) a drug retained by said polymer;

wherein said polymer is selected to be in a first contraction state, selected from the group consisting of contracted and relaxed bioelastomer states, when contacted with a physiological environment present in a human or animal to whom said composition is administered and wherein said polymer contains a reactive functional group that undergoes a reaction, either in the presence of said physiological environment or when said polymer is transported by a natural process in said human or animal to a location having a different physiological environment, to produce a second functional group, wherein the presence of said second functional group in said polymer causes said polymer to switch to the other of said contraction states, thereby making said drug available for release from said composition into said preselected physiological environment and wherein said polymer consists essentially of polypeptide elastomeric monomers, each of which comprises a β-turn, and wherein said pentapeptides are selected from the group consisting of VPGEG, IPGVG, IPGEG, VPGAG, VPGKG and VPAVG.

3. A drug delivery composition capable of selective release of said drug into a preselected physiological environment, comprising:

(1) a synthetic bioelastic polypeptide polymer comprising repeating elastomeric units selected from the group consisting of bioelastic pentapeptides, tetrapeptides, and nonapeptides, wherein said repeating units comprise amino acid residues selected from the group consisting of hydrophobic amino acid and glycine residues and wherein said repeating units exist in a conformation having a β-turn; and (2) a drug retained by said polymer;

wherein said polymer is selected to be in a first contraction state, selected from the group consisting of contracted and relaxed bioelastomer states, when contacted with a physiological environment present in a human or animal to whom said composition is administered and wherein said polymer contains a reactive functional group that undergoes a reaction, either in the presence of said physiological environment or when said polymer is transported by a natural process in said human or animal to a location having a different physiological environment, to produce a second functional group, wherein the presence of said second functional group in said polymer causes said polymer to switch to the other of said contraction states, thereby making said drug available for release from said composition into said preselected physiological environment and wherein said pentapeptides are of the formula $R_1PR_2R_3G$ and said tetrapeptides are of the formula $R_1PGG$ wherein $R_1$ is selected from the group consisting of Phe, Leu, Ile and Val; $R_2$ is selected from the group consisting of Gly and Ala; $R_3$ is selected from the group consisting of Phe, Leu, Ile and Val; P is proline; and G is glycine.

4. The composition of claim 1, wherein said polymer comprises multiple polypeptide elastomeric monomers, each of which comprises a β-turn, and further comprises intervening polypeptide segments between at least some elastomeric monomers.

5. The composition of claim 1, wherein said drug is covalently attached to said polymer.

6. The composition of claim 5, wherein said drug is attached to said polymer as a result of a chemical reaction between a first functional group in said drug and a second functional group in a side chain of an amino acid residue in said polymer.

7. The composition of claim 6, wherein (1) said first functional group is an amino group and said second functional group is a carboxyl group; (2) said first functional group is a carboxyl group and said second functional group is a hydroxyl, amino, or thiol group; (3) said first functional group is a thiol group and said second functional group is a thiol or carboxyl group; or (4) said first functional group is a hydroxyl group and said second functional group is a carboxyl group.

8. The composition of claim 6, wherein said first functional group is joined to said second functional group through a bifunctional bridging group.

9. The composition of claim 1, wherein said polypeptide comprises repeating units of the formula $\alpha P \rho \Omega G$ or $VP\theta\delta$, wherein:

V is a peptide-forming residue of L-valine;

P is a peptide-forming residue of L-proline;

G is a peptide-forming residue of glycine;

α is a peptide-forming residue of L-valine, L-leucine, L-isoleucine, L-phenylalanine or an ionizable peptide-forming residue selected from the group consisting of the residues of L-Glu, L-Asp, L-His, L-Lys, L-Tyr, and other ionizable peptide-forming L-amino acids;

ρ is a peptide-forming residue of glycine or a peptide-forming residue of D-Glu, D-Asp, D-His, D-Lys, D-Tyr, and other ionizable peptide forming D-amino acids;

Ω is a peptide-forming residue of L-valine, L-leucine, L-isoleucine, L-phenylalanine or an ionizable peptide-forming residue selected from the group consisting of the residues of L-Glu, L-Asp, L-His, L-Lys, L-Tyr, and other ionizable peptide-forming L-amino acids;

θ is a peptide-forming residue of D-Glu, D-Asp, D-His, D-Lys, D-Tyr, or another ionizable peptide forming D-amino acid; and δ is a peptide-forming residue of L-Glu, L-Asp, L-His, L-Lys, L-Tyr, or another ionizable peptide-forming L-amino acid.

10. The composition of claim 1, wherein said polymer has a composition selected to maintain said polymer in a contracted state when said polymer is contacted with said physiological condition.

11. The composition of claim 10, wherein said-polymer contains a first functional group that reacts in said physiological environment to form a second functional group, whereby the presence of said second functional group causes said polymer to switch from said contracted state to a relaxed state.

12. The composition of claim 11, wherein said drug is covalently attached to said polymer by a bond cleavable under said physiological environment.

13. The composition or claim 1, wherein said polymer has a composition selected to maintain said polymer is a relaxed state when said polymer is contacted with said physiological condition.

14. The composition of claim 10, wherein said polymer contains a first functional group that reacts when said polymer contacts said different physiological environment to form a second functional group, whereby the presence of said second functional group causes said polymer to switch from said relaxed state to a contracted state.

15. The composition of claim 14, wherein said polymer retains said drug without being convalently attached thereto and contact of said polymer with said different physiological environment causes said drug to be expelled from said composition.

16. The composition of claim 1, wherein said polymer is in the form of a nanosphere having a diameter of from 0.005 to 10 microns.

17. A drug delivery composition capable of selective release of said drug into a preselected physiological environment, comprising:
 (1) a synthetic bioelastic polypeptide polymer comprising repeating elastomeric units selected from the group consisting of bioelastic pentapeptides, tetrapeptides, and nonapeptides, wherein said repeating units comprise amino acid residues selected from the group consisting of hydrophobic amino acid and glycine residues and wherein said repeating units exist in a conformation having a β-turn; and
 (2) a drug retained by said polymer;
 wherein said polymer is selected to be in a first contraction state, selected from the group consisting of contracted and relaxed bioelastomer states, when contacted with a physiological environment present in a human or animal to whom said composition is administered and wherein said polymer contains a reactive functional group that undergoes a reaction, either in the presence of said physiological environment or when said polymer is transported by a natural process in said human or animal to a location having a different physiological environment, to produce a second functional groups, wherein the presence of said second functional group in said polymer causes said polymer to switch to the other of said contraction states, thereby making said drug available for release from said composition into said preselected physiological environment, wherein said drug is retained by said polymer without being covalently attached to said polymer.

18. The method of claim 17, wherein said composition is administered to said body by surgically implanting said composition in said body.

19. The method of claim 17, wherein said composition is administered to a first location in a body from which said composition is transported naturally to a second location in said body.

20. The method of claim 19, wherein said composition is administered directly into the blood stream of said body.

21. The method of claim 19, wherein said composition is administered orally.

22. The method of claim 19, wherein said composition is administered directly to the blood stream of said body in the form of a nanosphere of a size selected to penetrate the vascular bed of a tumor without penetrating normal tissue.

23. The method of claim 22, wherein said polymer has a composition selected to maintain said polymer is a relaxed state in said blood stream.

24. In a method of releasing a drug from a drug composition at a preselected rate and at a preselected location in a human or animal body, an improvement in said method which comprises:
 utilizing as said composition a drug delivery composition comprising
 (1) a synthetic bioelastic polypeptide polymer comprising repeating elastomeric units selected from the group consisting of bioelastic pentapeptides, tetrapeptides, and nonapeptides, wherein said repeating units comprise amino acid residues selected from the group consisting of hydrophobic amino acid and glycine residues and wherein said repeating units exist in a conformation having a β-turn; and
 (2) a drug retained by said polymer;
 wherein said polymer is selected to be in a first contraction state, selected from the group consisting of contracted and relaxed bioelastomer states, when contacted with physiological environment present in a human or animal to whom said composition is administered and wherein said polymer contains a reactive functional group that undergoes a reaction, either in the presence of said physiological environment or when said polymer is transported by a natural process in said human or animal to a different location having a different physiological environment, to produce a second functional group, wherein the presence of said second functional group in said polymer causes said polymer to switch to the other of said contraction states, thereby making drug available for release from said composition.

25. A method of releasing a drug from a drug composition at a preselected rate and at a preselected location in a human or animal body, an improvement which comprises:
 utilizing as said composition a drug delivery composition comprising
 (1) a synthetic bioelastic polypeptide polymer comprising repeating elastomeric units selected from the group consisting of bioelastic pentapeptides, tetrapeptides, and nonapeptides, wherein said repeating units comprise amino acid residues selected from the group consisting of hydrophobic amino acid and glycine residues and wherein said repeating units exist in a conformation having a β-turn; and
 (2) a drug retained by said polymer;
 wherein said polymer is selected to be in a first contraction state, selected from the group consisting of contracted and relaxed bioelastomer states, when contacted with a physiological environment present in a human or animal to whom said composition is administered and wherein said polymer contains a reactive functional group that undergoes a reaction, either in the presence of said physiological environment or when said polymer is transported by a natural process in said human or animal to a different location having a different physiological environment, to produce a second functional group, wherein the presence of said second functional group in said polymer causes said polymer to switch to the other of said contraction states, thereby making drug available for release from said composition; wherein said polymer retains said drug without being covalently attached thereto and contact of said polymer with a physiological environment causes said drug to be expelled from said polymer.

26. A drug delivery composition, comprising:
 (1) a synthetic bioelastic polypeptide polymer comprising repeating elastomeric units selected from the group consisting of bioelastic pentapeptides, tetrapeptides, and nonapeptides, wherein said repeating units comprise amino acid residues selected from the group consisting of hydrophobic amino acid and glycine residues and wherein said repeating units exist in a conformation having a β-turn; and
 (2) a drug retained by said polymer;
 wherein said polymer is selected to be in a first contraction state, selected from the group consisting of contracted and relaxed bioelastomer states, when contacted with a physiological environment present in a human or animal to whom said composition is administered which environment is capable of changing the inverse temperature transition point of said polymer and wherein said polymer contains a reactive functional group that undergoes a reaction, either in the presence of said physiological environment or when said polymer is transported by a natural process in said human or animal to a location having a different physiological environment, to produce a second functional group, wherein the presence of said second functional group in said polymer causes said polymer to switch to the other of said contraction states, thereby making said drug available for release from said composition.

27. A drug delivery composition capable of selective release of said drug into a preselected physiological environment, comprising:

(1) a synthetic bioelastic polypeptide polymer comprising repeating elastomeric units selected from the group consisting of bioelastic pentapeptides and tetrapeptides, wherein said repeating units comprise amino acid residues selected from the group consisting of hydrophobic amino acid and glycine residues and wherein said repeating units exist in a conformation having a β-turn of the formula:

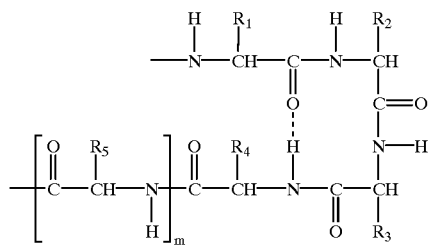

wherein $R_1$–$R_5$ represent side chains of amino acid residues 1–5, and m is 0 when said repeating unit is a tetrapeptide and 1 when said repeating unit is a pentapeptide; and (2) a drug retained by said polymer;

wherein said polymer is selected to be in a first contraction state, selected from the group consisting of contracted and relaxed bioelastomer states, when contacted with a physiological environment present in a human or animal to whom said composition is administered and wherein said polymer contains a reactive functional group that undergoes a reaction, either in the presence of said physiological environment or when said polymer is transported by a natural process in said human or animal to a location having a different physiological environment, to produce a second functional group, wherein the presence of said second functional group in said polymer causes said polymer to switch to the other of said contraction states, thereby making said drug available for release from said composition into said preselected physiological environment.

28. The composition of claim 27, wherein said hydrophobic amino acid residues are selected from the group consisting of alanine, valine, leucine, isoleucine, proline, phenylalanine, tryptophan, and methionine.

29. The composition of claim 28, wherein the first amino acid residue of said repeating units is a residue of valine, leucine, or isoleucine.

30. The composition of claim 28, wherein the second amino acid residue of said repeating units is a residue of proline.

31. The composition of claim 28, wherein the third amino acid residue of said repeating units is a residue of glycine.

32. The composition of claim 28, wherein the fourth amino acid residue of said repeating units is a residue of tryptophan or glycine.

33. The composition of claim 28, wherein said tetrapeptide is Val-Pro-Gly-Gly.

34. The composition of claim 28, wherein said pentapeptide is Val-Pro-Gly-Val-Gly.

* * * * *